(12) United States Patent
Kim et al.

(10) Patent No.: US 8,535,915 B2
(45) Date of Patent: Sep. 17, 2013

(54) PROMOTER, AND A PRODUCTION METHOD FOR L-LYSINE USING THE SAME

(75) Inventors: Chul Ha Kim, Seoul (KR); Jong Soo Choi, Seoul (KR); Sang Jo Lim, Incheon (KR); Hyung Joon Kim, Seoul (KR); So Yeon Rah, Seoul (KR); Gey Hang Jeon, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 299 days.

(21) Appl. No.: 12/864,979

(22) PCT Filed: Jan. 23, 2009

(86) PCT No.: PCT/KR2009/000382
§ 371 (c)(1),
(2), (4) Date: Jul. 28, 2010

(87) PCT Pub. No.: WO2009/096690
PCT Pub. Date: Aug. 6, 2009

(65) Prior Publication Data
US 2011/0076731 A1    Mar. 31, 2011

(30) Foreign Application Priority Data

Jan. 31, 2008    (KR) .................. 10-2008-0010073

(51) Int. Cl.
*C12P 13/08*    (2006.01)
*C12N 15/11*    (2006.01)
*C12N 1/21*    (2006.01)

(52) U.S. Cl.
USPC .... 435/115; 536/24.1; 435/320.1; 435/252.3; 435/252.32

(58) Field of Classification Search
None
See application file for complete search history.

(56) References Cited

U.S. PATENT DOCUMENTS

| | | | |
|---|---|---|---|
| 5,700,661 A | 12/1997 | Katsumata et al. | 435/69.1 |
| 5,965,391 A | 10/1999 | Reinscheid et al. | 435/69.1 |
| 6,221,636 B1 | 4/2001 | Hayakawa et al. | 435/115 |
| 6,746,855 B2 | 6/2004 | Kreutzer et al. | 435/115 |
| 6,927,046 B1 | 8/2005 | Hanke et al. | 435/106 |
| 7,141,388 B2 | 11/2006 | Crafton et al. | 435/69.1 |

FOREIGN PATENT DOCUMENTS

| | | |
|---|---|---|
| EP | 1 108 790 | 6/2001 |
| EP | 1 477 565 | 11/2004 |
| KR | 0159812 | 8/1998 |
| KR | 10-0397322 | 8/2003 |
| KR | 10-2006-0068505 | 6/2006 |
| KR | 10-2006-0079336 | 7/2006 |
| KR | 10-0620092 | 8/2006 |
| WO | 95/16042 | 6/1995 |
| WO | 01/66573 | 9/2001 |
| WO | 2008/033001 A1 | 3/2008 |

OTHER PUBLICATIONS

K.A. Barne et al. "Region 2.5 of the *Escherichia coli* RNA polymerase σ70 subunit is responsible for the recognition of the 'extended—10' motif at promoters" EMBO Journal 16(13):4034-4040 (1997).*
M. Liu et al. "A mutant spacer sequence between −35 and −10 elements makes the Plac promoter hyperactive and cAMP receptor protein-independent", PNAS 101(18): 6911-6916 (2004).*
Blombach et al., "Effect of pyruvate dehydrogenase complex deficiency on $_L$-lysine production with *Corynebacterium glutamicum*," *Appl. Microbiol. Biotechnol.* 76:615-623, 2007.
Ishino et al., "Nucleotide sequence of the *meso*-diaminopimelate D-dehydrogenase gene from *Corynebacterium glutamicum*," *Nucleic Acids Research* 15(9):3917, 1987.
Kim et al., "Cloning and Sequencing of the *ddh* Gene involved in the Novel Pathway of Lysine Biosynthesis from *Brevibacterium lactofermentum*," *Journal of Microbiology and Biotechnology* 5(5):250-256, 1995.
Schrumpf et al., "A Functionally Split Pathway for Lysine Synthesis in *Corynebacterium glutamicum*," *Journal of Bacteriology* 173(14):4510-4516, 1991.
Kawaguchi et al., "Engineering of an $_L$-arabinose metabolic pathway in *Corynebacterium glutamicum*," *Appl. Microbiol. Biotechnol.* 77:1053-1062, 2008.
Notification of Preliminary Rejection with English translation for corresponding Japanese Patent Application No. 2010-544884, dated Feb. 5, 2013, 6 pages.
Ishino et al., "Cloning and Sequencing of the *meso*-Diaminopimelate-D-dehydrogenase (*ddh*) Gene of Corynebacterium glutamicum," *Agric. Biol. Chem.* 52(11):2903-2909, 1988.
Yeh et al., "General organization of the genes specifically involved in the diaminopimelate-lysine biosynthetic pathway of *Corynebacterium glutamicum*," *Mol. Gen. Genet.* 212:105-111, 1988.

* cited by examiner

*Primary Examiner* — Rebecca E. Prouty
(74) *Attorney, Agent, or Firm* — Seed IP Law Group PLLC

(57) ABSTRACT

Disclosed are a nucleic acid molecule of *Corynebacterium glutamicum* origin, having an improved promoter activity, which is operably linked to a gene encoding diaminopimelate dehydrogenase, a vector containing the same, a transformant transformed with the vector, and a method for the production of L-lysine using the transformant.

10 Claims, 1 Drawing Sheet

PROMOTER, AND A PRODUCTION METHOD FOR L-LYSINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_1409USPC_SEQUENCE_LISTING.txt. The text file is 4 KB, was created on Nov. 12, 2010, and is being submitted electronically via EFS-Web.

TECHNICAL FIELD

The present invention relates to an improved promoter and a method for producing L-lysine using the same. More particularly, the present invention relates to a nucleic acid molecule of *Corynebacterium glutamicum* origin, showing improved promoter activity, which is operably linked to a gene encoding diaminopimelate dehydrogenase, a vector containing the nucleic acid molecule, a transformant with the vector introduced thereto, and a method for producing L-lysine using the transformant.

BACKGROUND ART

Coryneform bacteria are traditionally industrial microorganisms which are most widely used for the production of a variety of chemical materials useful in the animal feed, medicine and food industries, including amino acids, such as L-lysine, L-threonine, L-arginine, L-threonine and glutamic acid, and nucleic acid-related materials. These microorganisms are Gram-positive and require biotin for their growth. They are divided by snapping and their poor ability to degrade the metabolites they produce can be advantageously utilized. Representative examples of coryneform bacteria include *Corynebacterium* genus, such as *Corynebacterium glutamicum*, *Brevibacterium* genus, such as *Brevibacterium flavum*, *Athrobacter* spp. and *Microbacterium* spp. etc.

L-lysine is a commercially important L-amino acid which is used as a feed additive in animal nutrition thanks to its ability to help the body to absorb other amino acids thus improving the quality of the feedstuff. For the body, L-lysine is used as an ingredient of an injection solution, and also finds applications in the pharmaceutical field. Therefore, the industrial production of L-lysine is economically important industrial process.

The production yield of lysine is correlated with enzyme activity on the biosynthesis pathway which can be typically enhanced by amplifying one or more genes on the biosynthesis pathway of lysine or by employing a modified promoter for the genes. *Corynebacterium* strains with lysine biosynthesis-associated genes enhanced therein and the production of L-lysine using the same are well known. For example, U.S. Pat. No. 6,746,855 discloses a process for the production of L-lysine by fermenting an L-lysine producing *corynebacteria* with enhanced lysE gene (lysine export carrier gene), in which additionally genes selected from the group consisting of a dapA gene, an lysC gene, a pyc gene and a dapB gene are enhanced. U.S. Pat. No. 6,221,636 discloses *corynebacteria* transformed with a recombinant DNA comprising a nucleotide sequence coding for an aspartokinase in which feedback inhibition by L-lysine and L-threonine is substantially desensitized and a nucleotide sequence coding for a diaminopimelate decarboxylase.

Korean Patent No. 10-0345592 describes an *Escherichia* strain into which dapA and lysC, both modified to eliminate the feedback inhibition by L-lysine, are introduced and in which dapB and ddh genes are amplified, and a method for the production of L-lysine using the same.

For the development of coryneform bacteria into variants capable of producing target products at high titers, a genetic or metabolic engineering technique by which genes involved in the metabolism can be selectively controlled is needed. To this end, it is important to modify a promoter activity, a regulatory DNA region which provides a secure initial binding site for RNA polymerase to control the transcription of regulated genes.

Modified promoters originating from coryneform bacteria are found in many patents. For example, promoters from *corynebacterium* are described in U.S. Pat. No. 5,700,661 entitled "Gene expression regulatory DNA", U.S. Pat. No. 5,965,391 entitled "DNA which regulates gene expression in coryneform bacteria", U.S. Pat. No. 7,141,388 "Nucleotide sequences for transcriptional regulation in *corynebacterium glutamicum*", and Korean Patent No. 10-0653742 entitled "Novel L-lysine-inducible promoter", and a promoter from *Corynebacterium ammoniagenes* is described in Korean Patent Publication No. 10-2006-0068505 entitled "Novel promoter nucleic acid originating from *corynebacterium* genus bacteria, expression cassette comprising the promoter and vector comprising the cassette, host cell comprising the vector and method for expressing a gene using the cell".

However, none of the coryneform bacteria which are improved in the activity of ddh (diaminopimelate dehydrogenase) which plays a critical role in the lysine biosynthesis pathway, with an enhanced promoter for the enzyme substituted for the endogenous one on the genome of the host cell have been disclosed thus far.

DISCLOSURE

Technical Problem

Leading to the present invention, intensive and thorough research into the production of L-lysine, resulted in the finding that when being transformed with a ddh gene promoter, modified at particular bases, on the genome of *corynebacterium*, a *corynebacterium* genus microorganism shows diaminopimelate dehydrogenase activity improved over the endogenous activity.

Technical Solution

It is an object of the present invention to provide a nucleic acid molecule originating from *Corynebacterium glutamicum* which exhibits improved promoter activity.

It is another object of the present invention to provide a vector containing the nucleic acid molecule which exhibits improved promoter activity.

It is a further object of the present invention to provide a transformant with the vector anchored therein.

It is still a further object of the present invention to provide a method for producing L-lysine by fermenting the transformant.

Advantageous Effects

When being operably linked to a ddh gene, the nucleic acid molecule originating from *Corynebacterium glutamicum*, showing improved promoter activity, in accordance with the present invention shows higher promoter activity than does the wild-type promoter, and thus can increase diaminopimelate dehydrogenase activity. Therefore, the lysine-producing strain transformed with the nucleic acid molecule can produce lysine at higher yield.

BEST MODE

Figure 1:
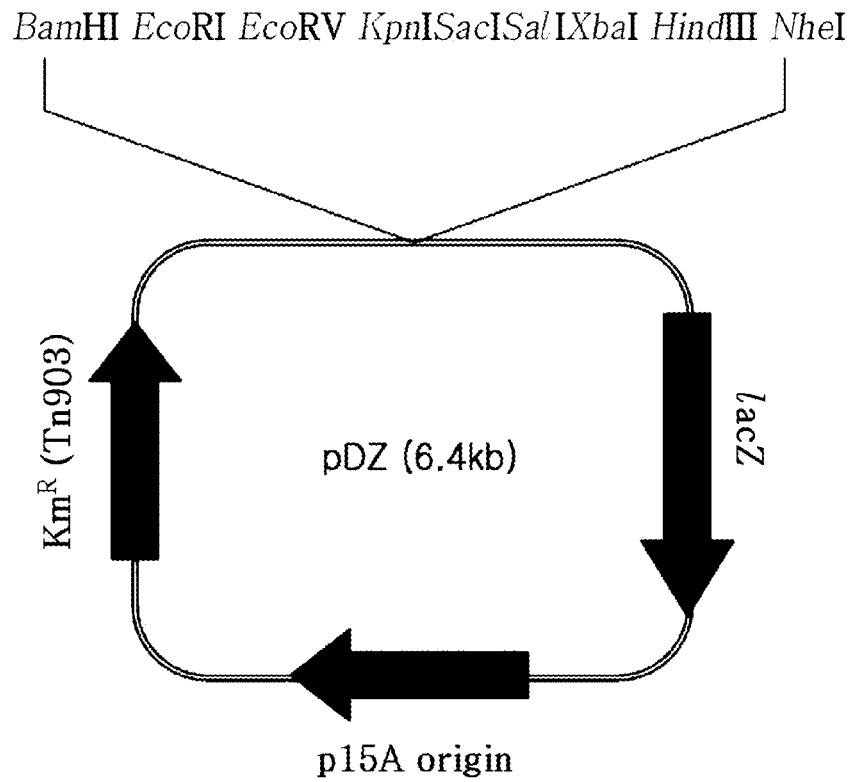
FIG. 1 is a diagram showing a genetic map of the vector pDZ for integration into a *corynebacterium* genome.

In accordance with an aspect thereof, the present invention pertains to a nucleic acid molecule of *Corynebacterium glutamicum* origin having a nucleotide sequence of SEQ ID NO. 2, which is operably linked to a gene encoding diaminopimelate dehydrogenase and exhibits improved promoter activity.

The term "promoter", as used herein, refers to a DNA region which contains an initial binding site for RNA polymerase and facilitates the transcription of a particular gene downstream thereof. That is, a promoter is an untranslated nucleotide sequence, upstream of a coding region, to which RNA polymerase binds to initiate the transcription of a gene, and is typically located near the genes it regulate, on the same strand and upstream (towards the 5' region of the sense strand).

The nucleic acid molecule of the present invention, originating from *Corynebacterium glutamicum*, having a promoter activity, is operably linked to a gene encoding diaminopimelate dehydrogenase. The ddh gene encoding diaminopimelate dehydrogenase plays an important role in the biosynthesis pathway of lysine in *Corynebacterium* spp.

The term "operably linked", as used herein, is intended to refer to a linkage between the nucleotide sequence having a promoter activity according to the present invention and the promoter sequence in such a functional relationship that the promoter can serve to initiate and mediate the transcription of a gene encoding diaminopimelate dehydrogenase. That is, when operably linked to a ddh gene, the nucleotide sequence having a promoter activity in accordance with the present invention can control the transcription activity of the ddh gene.

The nucleotide sequence having a promoter activity in accordance with the present invention, originating from a wild-type ddh gene promoter of *Corynebacterium glutamicum*, is modified to guarantee an enzymatic activity superior to the endogenous activity. The endogenous activity means an activity of enzyme in the wile type coryneform bacteria. Modification for guaranteeing higher promoter activity can be achieved using techniques well known in the art, preferably by inducing a mutation on the nucleotide sequence of the ddh gene promoter through deletion, insertion, non-conservative or conservative substitution or a combination thereof.

The nucleic acid molecule having a promoter activity in accordance with the present invention may be isolated or prepared using a standard biological technique. For example, PCR may be performed for isolation in the presence of proper primers. Alternatively, it may be synthesized with standard biological technique using an automated DNA synthesizer. In an embodiment, on the basis of a nucleotide sequence (SEQ ID NO. 1) containing a promoter region of a ddh gene (NCBI gene ID: NCg12528) obtained from the data of the NIH GenBank, four primers (SEQ ID NOS. 3~6) were synthesized. In the presence of the primers, PCR was performed to give a promoter-containing nucleic acid molecule which had modifications at particular base positions (SEQ ID NO. 2), with the genomic DNA of *Corynebacterium glutamicum* KFCC10881 serving as a template.

Preferably, the nucleic acid molecule having a *Corynebacterium glutamicum* promoter activity in accordance with the present invention is useful as a promoter for gene expression in prokaryotes, especially *E. coli* or coryneform bacteria. As used herein, the term "coryneform bacteria" refers to a microorganism belonging to the *Corynebacterium* genus or the *Brevibacterium* genus. Examples of coryneform bacteria useful in the present invention include, but are not limited to, *Corynebacterium glutamicum* ATCC13032, *Corynebacterium thermoaminogenes* FERM BP-1539, *Brevibacterium flavum* ATCC 14067, *Brevibacterium lactofermentum* ATCC 13869, and L-amino acid-producing mutants or strains originating therefrom, such as *Corynebacterium glutamicum* KFCC10881 and *Corynebacterium glutamicum* KFCC11001, with preference for *Corynebacterium glutamicum* KFCC 10881.

In accordance with another aspect thereof, the present invention pertains to a vector in which the nucleic acid molecule having an improved promoter activity is located.

As used herein, the term "vector" refers to a DNA construct in which a gene of interest is operably linked to a regulatory element so that the gene can be expressed in a proper host which anchors the vector therein. The regulatory element includes a promoter for initiating transcription, an operator for controlling transcription, a sequence coding for an mRNA ribosome-binding site, and a sequence for controlling the termination of transcription and translation.

So long as it is replicable in hosts, any vector known in the art may be employed in the present invention, without particular limitations. For example, the vector useful in the present invention may be a plasmid, a phage particle, or simply a potential genomic insert, but the present invention is not limited thereby. A preferable vector is pACYC177 (New England Biolab, GenBank accession #X06402). After being transformed into a suitable host, the vector may be replicated or perform its function irrespective of the host genome or may be integrated into the genome itself.

In greater detail, when the vector according to the present invention is introduced into a host cell, the nucleic acid molecule having the promoter activity in the vector may undergo homologous recombination with a promoter region for an endogenous ddh gene on the host genome, resulting in the integration of the vector into the chromosome of the host cell. Therefore, the vector according to the present invention may further comprise a selection marker for indicating the insertion of the vector into the host chromosome. Adapted to indicate a cell transformed with the vector, that is, whether a gene of interest is inserted into the genome of the host cell, the selection marker may endow the cell with ability to show drug resistance, cytotoxic agent resistance, auxotrophy, or selectable phenotype expression such as the expression of a surface protein. In the presence of a selective agent, transformed cells may be selected because only the cells which express the selection marker rendering survive or show another phenotype. Preferably, the vector may comprise a lacZ gene as a selection marker.

Figure 2:
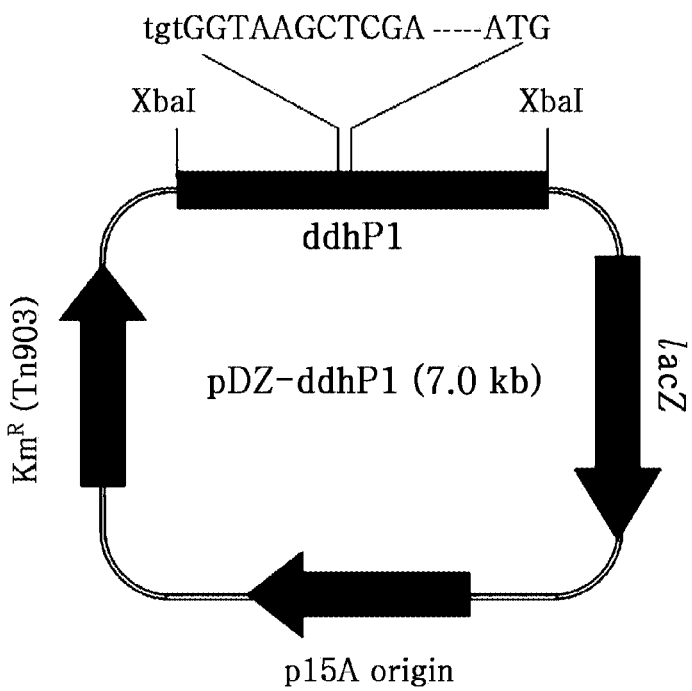
FIG. 2 is a diagram showing a genetic map of the vector pDZ-ddhP1 for promoter replacement.

In an embodiment of the present invention, a vector is constructed to contain a modified ddh promoter improved in activity which can be substituted for the endogenous ddh promoter of *Corynebacterium glutamicum* through homologous recombination. To this end, first, the vector pACYC177 for *E. coli* cloning is digested with restriction enzymes and blunt ended with Klenow fragment. Separately, a nucleotide sequence comprising a lacZ gene and its promoter is amplified from the genomic DNA of *E. coli* K12W3110 through PCR. These two DNA fragments thus obtained are ligated to each to give a circular nucleic acid molecule, followed by inserting an adaptor sequence containing multiple restriction enzyme sites therein into the circular nucleic acid molecule to afford the vector pDZ for insertion into the chromosome of *Corynebacterium* (FIG. 1). Thereafter, a ddh gene promoter modified at particular bases to show high activity is inserted into the adaptor sequence of the pDZ vector to give the vector pDZ-ddhP1 comprising the nucleotide sequence of SEQ ID NO. 2 (FIG. 2).

In accordance with a further aspect thereof, the present invention pertains to a transformant with the vector anchored therein.

The term "transformation", as used herein, refers to the introduction of an exogenous DNA material into a host cell in which the exogenous DNA material is replicable as an element separated from or incorporated into the host genome. Resulting from the transformation of the vector into a host cell, the transformant anchors the vector in the form of a plasmid or as is incorporated into the chromosome of the host cell after the nucleotide sequence having a promoter activity undergoes homogenous recombination with an endogenous promoter region for a ddh gene on the genome of the host cell.

So long as it is used to introduce the vector of the present invention into a host cell, any technique may be employed in the present invention. Depending on a host cell, a suitable standard technique may be selected, for example, among electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique.

It is useful to use a host cell which is highly efficient in the uptake and expression of foreign DNA materials, and it can be applicable to all microorganism including prokaryote and eukaryote. Preferably, *E. coli* or coryneform bacteria may be used, and more preferable is *Corynebacterium glutamicum* KFCC10881.

In the cells transformed with the vector of the present invention, the modified promoter having improved activity is substituted for the endogenous promoter through homologous recombination, potentiating the mRNA level of the ddh gene. As a result, the transformant has higher diaminopimelate dehydrogenase activity than dose the wild-type.

In an embodiment of the present invention, the vector pDZ-ddhP1 in which the promoter having a nucleotide sequence of SEQ ID NO. 2 in accordance with the present invention was harbored was transformed into *Corynebacterium glutamicum* KFCC10881 to give a transformant (KFCC10881-ddhP1), named CA01-0136, showing improved diaminopimelate dehydrogenase activity, which was then deposited under the terms of the Budapest Treaty with the Korean Culture Center of Microorganisms (hereinafter referred to as "KCCM"). Eulim Building, Hongie-1-Dong, Seodaemun-Ku, Seoul. 361-221. Korea) under Accession Number KCCM10920P on Jan. 18, 2008.

In accordance with a further aspect thereof, the present invention pertains to a method for the production of lysine comprising the fermentation of the transformant.

Compared to the wild-type, the transformant according to the present invention is improved in diaminopimelate dehydrogenase activity. Because diaminopimelate dehydrogenase is the most essential enzyme on the biosynthesis pathway of lysine, the fermentation of the transformant leads to the production of lysine at higher yield.

In the present invention, the fermentation of the transformant may be conducted using a well-known method, and conditions for the fermentation, including temperature, time, pH, etc. may be controlled properly. A detailed description is given of the fermentation in the following document [Chmiel; Bioprozesstechnik 1. Einfuhrung in die Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)]. The fermentation may be achieved by batch cultivation, continuous cultivation or fed-batch cultivation. Preferably, a fed batch or repeated fed batch process is used in a continuous manner for the fermentation, but the present invention is not limited thereto.

For use in the fermentation, a medium must satisfy the requirement of the strain employed. Culture media suitable for use in culturing various microorganisms are well known in the art (e.g., "Manual of Methods for General Bacteriology" from American Society for Bacteriology (Washington D.C., USA, 1981)). Culture media may contain as carbon sources saccharides and carbohydrates (e.g., glucose, sucrose, lactose, fructose, maltose, molasse, starch and cellulose), lipids and fats (e.g., soybean oil, sunflower seed oil, peanut oil and coconut oil), fatty acids (e.g., palmitic acid, stearic acid, rinoleic acid), alcohols (e.g., glycerol and ethanol) and organic acids (e.g., acetic acid). These materials may be used in separation or in combination. As nitrogen sources, nitrogen-containing organic compounds (e.g., peptone, yeast extract, broth, malt extract, corn steep liquor, soybean meal and urea), or inorganic compounds (e.g., ammonium sulfate, ammonium chloride, ammonium phosphate, ammonium carbonate and ammonium nitrate) may be used in separation or in combination. Examples of phosphorus sources useful in the culture media include dipotassium hydrogen phosphate, potassium dihydrogen phosphate and corresponding sodium salts.

Also, culture media may contain metal salts essential to the growth of cells (e.g., magnesium sulfate or ferrous sulfate) and may be supplemented with essential nutrients for stimulating growth such as amino acids and vitamins. In addition, proper precursors may be added to the culture media. The nutrients or supplements may be added altogether once or in separation during fermentation.

The pH of the culture media may be adjusted with an alkaline compound (e.g., sodium hydroxide, potassium hydroxide or ammonia) or an acidic compound (e.g., phosphoric acid or sulfuric acid). The generation of foams in culture media may be restrained using an anti-foaming agent such as fatty acid polyglycol ester. The culture media may be kept under an aerobic condition by introducing oxygen or an oxygen-containing gas mixture thereinto. As to the culture temperature, it is typically between 20 and 45° C. and preferably between 25 and 40° C. The fermentation is continued until a maximal amount of L-amino acid is produced. In this regard, it may be accomplished within 10 to 160 hrs. After being produced, the L-lysine may be exported into the culture media or may remain within the cells.

Alternatively, the method for the production of lysine in accordance with the present invention may further comprise collecting the produced lysine. L-lysine can be isolated from culture media or cells using a well-known method. Examples of the collecting method useful in the present invention include filtration, anionic exchange chromatography, crystallization and HPLC, but are not limited thereto.

A better understanding of the present invention may be obtained through the following examples which are set forth to illustrate, but are not to be construed as limiting the present invention.

MODE FOR INVENTION

In the following examples, a recombinant vector was constructed to contain a promoter for a ddh gene of *Corynebacterium glutamicum* which was modified to have improved activity. The recombinant vector was transformed into *Corynebacterium glutamicum* KFCC10881 in which the modified ddh promoter was then incorporated into the genome of the cell by homologous recombination with the endogenous promoter, resulting in a novel strain capable of producing lysine at higher yield.

Artificially mutated from a *Corynebacterium glutamicum* wild-type strain (ATCC13032), *Corynebacterium glutamicum* KFCC10881 useful in the present invention was resistant to S-(2-aminoethyl) cysteine (hereinafter referred to as "AEC") and homoserine leaky (Korean Patent Nos. 0159812 and 0397322).

EXAMPLE 1

Construction of Recombinant Vector Containing Improved Promoter (1) Construction of a Vector for Integration into Genome (pDZ)

In this example, pDZ, a vector to be integrated into *Corynebacterium* genome, was constructed on the basis of pACYC177 (New England Biolab, GenBank accession # X06402), a vector for use in *E. coli*.

After being treated with AcuI and BanI, the pACYC177 vector was blunt ended with a Klenow fragment. For the use as a selection marker, a lacZ gene originating from *E. coli* was prepared by amplifying a genomic DNA of *E. coli* K12 W3110 comprising the gene and its promoter through PCR, followed by treating the PCR product with T4 DNA polymerase and polynucleotide kinase to phosphorylate at 5' end and make the opposite ends blunt, respectively. The two DNA fragments thus obtained were ligated to each other to give a circular nucleic acid molecule into which an artificially synthesized adaptor sequence containing a plurality of restriction enzyme sites was then inserted to afford the vector pDZ for insertion into the chromosome of *Corynebacterium*. In FIG. 1, the pDZ vector for integration into *Corynebacterium* chromosome is schematically illustrated.

(2) Construction of a Vector Containing an Improved Promoter for ddh Gene

In this example, a recombinant vector was constructed to contain an improved promoter for a ddh gene of the lysine-producing strain *Corynebacterium glutamicum*.

On the basis of the data of the NIH GenBank, first, a nucleotide sequence (SEQ ID NO. 1) comprising a promoter region for the ddh gene (NCBI ID No. NCgl2528) was obtained. From this nucleotide sequence was prepared a DNA fragment which was mutated at particular base positions. Each modified promoter sequence was designed on the basis of a typical consensus promoter sequence found in microorganisms.

For use in the preparation of the modified promoter sequences, four primers (SEQ ID NOS. 3~6, Table 1) were synthesized based on the base sequences.

TABLE 1

| Primer | Nucleotide Sequence | SEQ ID NO. |
|---|---|---|
| ddh/PF | CCG GGG ATC CTC TAG AGT GCG TGG CGA GTT TTA CAA AG | 3 |
| ddh/PR | GCA GGT CGA CTC TAG AGG CGA ACT GCG CGA ACT TTG G | 4 |
| ddh/P1F | TAT GCA TTG TGG TAA GCT CG | 5 |
| ddh/P1R | CGA GCT TAC CAC AAT GCA TA | 6 |
| ddh/P1mut | CTA AGT ATG CAT TGT | 7 |

A promoter sequence for the ddh gene of *Corynebacterium glutamicum* was prepared by PCR using sets of the primers of Table 1 in the presence of PfuUltra™ High-Fildelity DNA Polymerase (Stratagene) with the genomic DNA of *Corynebacterium glutamicum* KFCC10881 serving as a template. PCR was performed with 30 cycles of denaturation at 96° C. for 30 sec, annealing at 53° C. for 30 sec and extension at 72° C. for 30 sec. As a result, the PCR product was 300 bp long DNA fragment with the substitution portion located at one terminal region. ddhP1-1 was amplified with a set of the primers of SEQ ID NOS. 3 and 6, and ddhP1-2 with a set of the primers of SEQ ID NOS. 5 and 4. The PCR product was digested with XBaI, and cloned into pDZ using an In-fusion Cloning Kit (TAKARA) to afford the recombinant vector pDZ-ddhP1.

FIG. 2 is a map of the vector pDZ-ddhP1 containing the promoter sequence of SEQ ID NO.2 which is integrated into *Corynebacterium* genome.

EXAMPLE 2

Introduction of the Recombinant Vector into *Corynebacterium glutamicum* Strains In this example, the recombinant vector prepared above was introduced into the lysine-producing strain *Corynebacterium glutamicum* KFCC-10881, so that the modified ddh promoter sequence on the vector was integrated into the genome of the cell through homologous recombination with the endogenous ddh promoter on the genome.

To this end, the recombinant vector pDZ-ddhP1 containing the DNA fragment corresponding to the modified promoter sequence was transformed into *Corynebacterium glutamicum* KFCC10881 using an electroporation method (based on Appl. Microbiol. Biotechnol. (1999) 52:541-545), followed by selecting on a selection medium containing kanamycin in an amount of 25 mg/L the transformants in which the modified promoter was integrated into the genome through homologous recombination with the endogenous promoter.

Success in the insertion of the vector into the genome was identified by the appearance of a blue color on the plate containing X-gal (5-bromo-4-chloro-3-indolyl-β-D-galactoside). Single crossovers with the vector incorporated into the genome thereof were cultured in a nutrient broth with agitation (30° C., 8 hrs) after which the culture was diluted to a concentration of from $10^{-4}$ to $10^{-10}$ before being spread over plates containing X-gal. While most of the colonies grown on the plates appeared blue, only a low proportion of the colonies remained white. The white colonies were selected as double-crossover colonies which anchored the ddh promoter which was mutated at particular base positions. For confirmation, the selected strains were examined for base substitution by PCR and base sequenced. The strain transformed with pDZddhP1 was examined for base substitution in the promoter, using a set of primers of SEQ ID NOS. 4 and 7, by PCR and base sequencing.

The lysine-producing strain *Corynebacterium glutamicum* KFCC10881-ddhP1 in which the ddh promoter mutated at particular base positions was integrated into the genome thereof was finally confirmed through double crossover.

EXAMPLE 3

Assay of the ddh Promoter-Improved Strain for Diaminopimelate Dehydrogenase Activity The mother strain *Corynebacterium glutamicum* KFCC10881 and the L-lysine-producing strain *Corynebacterium glutamicum* KFCC10881-ddhP1 finally prepared in Example 2 were cultured, and proteins were isolated from the cultures and assayed for diaminopimelate dehydrogenase activity, as follows.

Each of the cultures grown to the logarithm phase was inoculated into 50 mL of the following seed medium (I) to give an $OD_{600}$ of 0.3, and then incubated until the optical density at 600 nm reached about 15. After being collected through centrifugation (5,000 rpm, 15 min), cell mass was washed twice with 20 mM Tris HCl (pH 8.0) and suspended in the same buffer to an optical absorbance at 610 nm of turbidity 160. Cells were disrupted for 6 min in a glass beater with glass beads added at 1.25 g/1.5 ml of the suspension. After centrifugation (15,000 rpm, 20 min), the supernatant was quantitatively measured for protein content by a Bradford method (Bradford, M. M 1976. Anal. Biochem. 72:248-254) and used as a crude protein solution for measuring the activity of diaminopimelate dehydrogenase.

In order to quantify the activity of diaminopimelate dehydrogenase, about 0.01 mL of the crude protein solution was mixed with a reaction solution containing 0.2 M Glycine/NaOH (pH 10.5), 2 mM NADP and 4 mM meso-diaminopimelate to give a total volume of 1 mL and allowed to react at 25° C. for 10 min during which absorbances at 340 nm were monitored. The activity of diaminopimelate dehydrogenase was defined as μmoles of the NADPH reduced per min by 1 mg of protein and expressed in unit (U).

*Corynebacterium glutamicum* KFCC10881-ddhP1 was observed to have a diaminipimelate dehydrogenase activity 23.2-fold higher than that of the mother strain KFCC10881 (Table 2).

TABLE 2

| Strain | Diaminopimelate Dehydrogenase (U) | Folds |
|---|---|---|
| KFCC10881 | 25.2 | 1 |
| KFCC10881-ddhP1 | 584.5 | 23.2 |

Seed Medium (I) (pH 7.0)

Glucose 20 g, Polypeptone 10 g, Yeast extract 5 g, $(NH_4)_2SO_4$ 5 g, Urea 1.5 g, $KH_2PO_4$ 4 g, $K_2HPO_4$ 8 g, $MgSO_4$ $7H_2O$ 0.5 g, Biotin 150 μg, Thiamine HCl 1500 μg, Calcium pantothenate 3000 μg, Nicotine amide 3000 μg (per liter of distilled water)

EXAMPLE 4

Lysine Production in the ddh Promoter-Improved Strain

The mother strain *Corynebacterium glutamicum* KFCC10881 and the L-lysine-producing strain *Corynebacterium glutamicum* KFCC10881-ddhP1 prepared in Example 2 were fermented to produce L-lysine, as follows.

*Corynebacterium glutamicum* KFCC-10881 and KFCC10881-ddhP1 were inoculated into 250 mL corner-baffle flasks, each containing 25 mL of the following seed medium (II), and cultured at 30° C. for 20 hrs with shaking at 200 rpm. To 24 mL of the following production medium in a 250 mL corner-baffle flask was added 1 mL of the seed culture, followed by incubation at 30° C. for 120 hrs with shaking (200 rpm).

After the completion of culture, HPLC analysis was performed to determine the amounts of the L-lysine produced by the strains. The concentrations of L-lysine in the cultures of *Corynebacterium glutamicum* KFCC-10881 and KFCC-10881-ddhP1 are summarized in Table 3, below.

TABLE 3

| | Lysine (g/l) | | |
|---|---|---|---|
| Strain | Batch 1 | Batch 2 | Batch 3 |
| KFCC10881 | 43.2 | 42.5 | 42.5 |
| KFCC10881-ddhP1 | 44.2 | 44.2 | 44.1 |

Seed Medium (II) (pH 7.0)

Raw sugar 20 g, Peptone 10 g, Yeast extract 5 g, Urea 1.5 g, $KH_2PO_4$ 4 g, $K_2HPO_4$ 8 g, $MgSO_4$ $7H_2O$ 0.5 g, Biotin 100 μg, Thiamine HCl 1000 μg, Calcium pantothenate 2000 μg, Nicotine amide 2000 μg (per liter of distilled water)

Production Medium (pH 7.0)

Glucose 100 g, $(NH_4)_2SO_4$ 40 g, Soybean protein 2.5 g, Corn steep solids 5 g, Urea 3 g, $KH_2PO_4$ 1 g, $MgSO_4$ $7H_2O$ 0.5 g, Biotin 100 μg, Thiamine chloride 1000 μg, Calcium pantothenate 2000 μg, Nicotine amide 3000 μg, $CaCO_3$ 30 g (per liter of distilled water)

As seen in Table 3, *Corynebacterium glutamicum* KFCC-ddhP1 with 23-fold improved diaminipimelate dehydrogenase activity was found to increase in lysine productivity by about 3%, compared with the mother strain KFCC10881.

[Industrial Applicability]

Having higher promoter activity than that of the wild-type, as described hitherto, the nucleic acid molecule of *Corynebacterium glutamicum* origin according to the present invention can enhance diaminopimelate dehydrogenase activity, thus increasing the biosynthesis efficiency of lysine. Consequently, the strain which anchors the improved promoter can produce L-lysine, an industrially important amino acid, at high yield.

The invention claimed is:

1. A nucleic acid molecule comprising the promoter portion of SEQ ID NO. 2.

2. A vector, comprising the nucleic acid molecule of claim 1.

3. The vector according to claim 2, being pDZ-ddhP1 having a genetic map of FIG. 2.

4. A transformant, harboring the vector of claim 2.

5. The transformant according to claim 4, belonging to Corynebacterium genus or Brevibacterium genus.

6. The transformant according to claim 4, being named CA01-0136, with Accession No. KCCM10920P.

7. The transformant according to claim 4, wherein the nucleic acid molecule of claim 1 is incorporated into a genome of the transformant through homologous recombination.

8. The transformant according to claim 4, harboring the molecule of claim 1 as a plasmid.

9. A method for producing lysine, comprising:
preparing an expression vector comprising the nucleic acid molecule of claim 1 and a gene encoding diaminopimelate dehydrogenase, wherein the gene is operably linked to the nucleic acid molecule:
transforming the resulting vector into a microorganism belonging to a Corynebacterium genus or a Brevibacterium genus, and
fermenting the resulting transformant to thereby produce lyine.

10. The method according to claim 9, wherein the transformant is Corynebacterium glutamicum CA01-0136 with Accession No. KCCM10920P.

* * * * *

SEQUENCE LISTING

<160> NUMBER OF SEQ ID NOS: 7

<210> SEQ ID NO 1
<211> LENGTH: 603
<212> TYPE: DNA
<213> ORGANISM: Corynebacterium glutamicum

```
<220> FEATURE:
<221> NAME/KEY: gene
<222> LOCATION: (1)..(603)
<223> OTHER INFORMATION: ddh promoter and some portion of ddh gene

<400> SEQUENCE: 1
gccgtgcgtg gcgagtttta caaagaaccc cacatcatca atgcctaaat ggcgggtatt      60
ttcatccaaa cccaaccgcg catcattcca atgctgatcc accccatccg gataaaccac     120
catgaacggc aacggatcaa aagtcctgtt ggtgaagctg cgcccacag atcctgactg      180 ctgggagcca tgaaaataga tcagcgcatc cgtggtggaa ccaaaaggct caacaatacg     240
aaacgttcgc tttcggtcct gatgaaagag atgtccctga atcatcatct aagtatgcat     300
ctcggtaagc tcgaccagga cagtgccacc acaattttgg aggattacaa gaacatgacc     360
aacatccgcg tagctatcgt gggctacgga aacctgggac gcagcgtcga aaagcttatt     420
gccaagcagc ccgacatgga ccttgtagga atcttctcgc gccgggccac cctcgacaca     480
aagacgccag tctttgatgt cgccgacgtg gacaagcacg ccgacgacgt ggacgtgctg     540
ttcctgtgca tgggctccgc caccgacatc cctgagcagg caccaaagtt cgcgcagttc     600
gcc                                                                    603

<210> SEQ ID NO 2
<211> LENGTH: 603
<212> TYPE: DNA
<213> ORGANISM: Corynebacterium glutamicum
<220> FEATURE:
<221> NAME/KEY: gene
<222> LOCATION: (1)..(603)
<223> OTHER INFORMATION: ddhP1 promoter and some portion of ddh gene

<400> SEQUENCE: 2
gccgtgcgtg gcgagtttta caaagaaccc cacatcatca atgcctaaat ggcgggtatt      60
ttcatccaaa cccaaccgcg catcattcca atgctgatcc accccatccg gataaaccac     120
catgaacggc aacggatcaa aagtcctgtt ggtgaagctg cgcccacag atcctgactg      180 ctgggagcca tgaaaataga tcagcgcatc cgtggtggaa ccaaaaggct caacaatacg     240
aaacgttcgc tttcggtcct gatgaaagag atgtccctga atcatcatct aagtatgcat     300
tgtggtaagc tcgaccagga cagtgccacc acaattttgg aggattacaa gaacatgacc     360
aacatccgcg tagctatcgt gggctacgga aacctgggac gcagcgtcga aaagcttatt     420
gccaagcagc ccgacatgga ccttgtagga atcttctcgc gccgggccac cctcgacaca     480
aagacgccag tctttgatgt cgccgacgtg gacaagcacg ccgacgacgt ggacgtgctg     540
ttcctgtgca tgggctccgc caccgacatc cctgagcagg caccaaagtt cgcgcagttc     600
gcc                                                                    603

<210> SEQ ID NO 3
<211> LENGTH: 38
<212> TYPE: DNA
<213> ORGANISM: Artificial Sequence
<220> FEATURE:
<223> OTHER INFORMATION: primer ddh/PF

<400> SEQUENCE: 3
ccggggatcc tctagagtgc gtggcgagtt ttacaaag                               38

<210> SEQ ID NO 4
<211> LENGTH: 37
<212> TYPE: DNA
<213> ORGANISM: Artificial Sequence
```

```
<220> FEATURE:
<223> OTHER INFORMATION: primer ddh/PR

<400> SEQUENCE: 4
gcaggtcgac tctagaggcg aactgcgcga actttgg                              37

<210> SEQ ID NO 5
<211> LENGTH: 20
<212> TYPE: DNA
<213> ORGANISM: Artificial Sequence
<220> FEATURE:
<223> OTHER INFORMATION: primer ddh/P1F

<400> SEQUENCE: 5
tatgcattgt ggtaagctcg                                                 20

<210> SEQ ID NO 6
<211> LENGTH: 20
<212> TYPE: DNA
<213> ORGANISM: Artificial Sequence
<220> FEATURE:
<223> OTHER INFORMATION: primer ddh/P1R

<400> SEQUENCE: 6
cgagcttacc acaatgcata                                                 20

<210> SEQ ID NO 7
<211> LENGTH: 15
<212> TYPE: DNA
<213> ORGANISM: Artificial Sequence
<220> FEATURE:
<223> OTHER INFORMATION: primer ddh/P1mut

<400> SEQUENCE: 7
ctaagtatgc attgt                                                      15
```